(12) United States Patent
McCaig et al.

(10) Patent No.: US 9,423,387 B2
(45) Date of Patent: Aug. 23, 2016

(54) LOCALIZED DEPOSITION OF POLYMER FILM ON NANOCANTILEVER CHEMICAL VAPOR SENSORS BY SURFACE-INITIATED ATOM TRANSFER RADICAL POLYMERIZATION

(75) Inventors: Heather McCaig, Pasadena, CA (US); Edward B. Myers, Sherman Oaks, CA (US); Michael L. Roukes, Pasadena, CA (US); Nathan S. Lewis, La Canada, CA (US); Derrick Chi, Walnut, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 1074 days.

(21) Appl. No.: 13/419,510

(22) Filed: Mar. 14, 2012

(65) Prior Publication Data

US 2013/0098141 A1  Apr. 25, 2013

Related U.S. Application Data

(60) Provisional application No. 61/452,849, filed on Mar. 15, 2011.

(51) Int. Cl.
*G01N 33/00* (2006.01)
*G01N 5/02* (2006.01)
*G01N 9/00* (2006.01)

(52) U.S. Cl.
CPC .............. *G01N 33/0027* (2013.01); *G01N 5/02* (2013.01); *G01N 9/002* (2013.01)

(58) Field of Classification Search
CPC ................ G01N 2291/0256; G01N 29/036; G01N 29/022; G01N 19/10; G01N 2291/0267; G01N 33/0027; G01N 5/02; G01N 9/002; B81C 1/00206; H01L 41/1136
See application file for complete search history.

(56) References Cited

U.S. PATENT DOCUMENTS

| | | | |
|---|---|---|---|
| 8,168,291 B2 * | 5/2012 | Shah et al. | 428/293.4 |
| 2003/0045019 A1 * | 3/2003 | Kubena | 438/49 |
| 2005/0276726 A1 * | 12/2005 | McGill et al. | 422/96 |
| 2009/0061533 A1 * | 3/2009 | Minami et al. | 436/518 |
| 2010/0209301 A1 * | 8/2010 | Hartmann-Thompson | 422/83 |

OTHER PUBLICATIONS

Lang, Nanomechanical Cantilever Array Sensors, Springer 2010, p. 428.*
Barbey et al., "Polymer Brushes via Surface-Initiated Controlled Radical Polymerization: Synthesis, Characterization, Properties, and Applications", *Chemical Reviews* 2009, 109 (11), 5437-5527.

(Continued)

*Primary Examiner* — Daniel S Larkin
*Assistant Examiner* — Jamar Ray
(74) *Attorney, Agent, or Firm* — The Marbury Law Group, PLLC

(57) ABSTRACT

Cantilever chemical vapor sensors that can be tailored to respond preferentially in frequency by controlling the location of deposition of an adsorbing layer. Cantilever chemical vapor sensor having a base, one or more legs and a tip are fabricated using a gold layer to promote deposition of a sorbing layer of a polymeric material in a desired location, and using a chromium layer to inhibit deposition of the sorbing layer in other locations. Sorbing layers having different glass temperatures Tg and their effects are described. The methods of making such cantilever chemical vapor sensors are described.

14 Claims, 16 Drawing Sheets

(56) References Cited

OTHER PUBLICATIONS

Bietsch et al., "Rapid functionalization of cantilever array sensors by inkjet printing", *Nanotechnology* 2004, 15 (8), 873-880.

Bradley et al., "Response Characteristics of Thermoresponsive Polymers Using Nanomechanical Cantilever Sensors", *Macromol. Chern. Phys.* 2009, 210 (16), 1339-1345.

Bumbu et al., "Synthesis and characterization of polymer brushes on micromechanical cantilevers", *Macromol. Chern. Phys.* 2004, 205 (13), 1713-1720.

Bumbu et al., "Micromechanical cantilever technique: A tool for investigating the swelling of polymer brushes", *Langmuir*, 2007, 23 (4), 2203-2207.

Chen, et al., "Adsorption-induced surface stress and its effects on resonance frequency of microcantilevers" *Journal of Applied Physic*, 1995, 77 (8), 3618-3622.

Jones et al., "Controlled surface-initiated polymerizations in aqueous media", *Adv. Mater.* 2001, 13 (16), 1256-1259.

Matyjaszewski et al., Polymers at interfaces: Using atom transfer radical polymerization in the controlled growth of homopolymers and block copolymers from silicon surfaces in the absence of untethered sacrificial initiator. *Macromolecules* 1999,32 (26), 8716-8724.

Salaita et al., "Applications of dip-pen nanolithography", *Nat. Nanotechnol.* 2007, 2 (3), 145-155.

Thundat et al., "Detection of Mercury Vapor Using Resonating Microcantilevers", *Applied Physics Letters* 1995, 66 (13),1695-1697.

Wright, et al., Study of microcapillary pipette-assisted method to prepare polyethylene glycol-coated microcantilever sensors. *Sensors and Actuators B-Chemical*, 2005, 107 (1), 242-251.

Xu, et al., Effect of block length on solvent response of block copolymer brushes: Combinatorial study with block copolymer brush gradients. *Macromolecules* 2006, 39 (9), 3359-3364.

Yang, et al., "Zeptogram-Scale Nanomechanical Mass Sensing", *Nano Lett.*, vol. 6, No. 4, 2006.

\* cited by examiner

Passivation

Initiator SAM

SI-ATRP

LOCALIZED DEPOSITION OF POLYMER FILM ON NANOCANTILEVER CHEMICAL VAPOR SENSORS BY SURFACE-INITIATED ATOM TRANSFER RADICAL POLYMERIZATION

CROSS-REFERENCE TO RELATED APPLICATIONS

This application claims priority to and the benefit of U.S. provisional patent application Ser. No. 61/452,849, filed Mar. 15, 2011, which application is incorporated herein by reference in its entirety.

STATEMENT REGARDING FEDERALLY FUNDED RESEARCH OR DEVELOPMENT

This invention was made with government support under 2008-ST-061-ED0002 awarded by the Department of Homeland Security. The government has certain rights in the invention.

FIELD OF THE INVENTION

The invention relates to chemical vapor sensors in general and particularly to chemical vapor sensors that employ nanocantilevers.

BACKGROUND OF THE INVENTION

Nanoelectromechanical systems (NEMS) resonator chemical vapor sensors operate by detecting the sorption of vapor molecules through a shift in resonant frequency. The resonant frequency of NEMS resonators depends both on the mass and stiffness of the device. Upon vapor sorption, both the mass and the stiffness of the device can change. For nanocantilevers, which are one class of NEMS resonators, these factors act in opposite directions with mass loading decreasing the resonance frequency and stiffening increasing the resonance frequency. Further, vapor sorption on the nanocantilever tip is strongly mass loading and minimally stiffening, while vapor sorption at the clamped end is strongly stiffening and minimally mass loading. The resonant behavior of the sensors can be observed using any of static (e.g., displacement) mode or dynamic (e.g., vibratory) mode measurements performed by way of optical frequency sensing, electrical or electronic sensing (for example radio frequency sensing or piezoresistive sensing), or acoustic frequency sensing. It has been shown that NEMS sensors can measure changes in mass at the level of zeptograms (Y. T. Yang, et al., Zeptogram-Scale Nanomechanical Mass Sensing, Nano Lett., Vol. 6, No. 4, 2006).

NEMS chemical vapor sensors are made more sensitive and selective through deposition of polymer films or self assembled monolayers (SAMs). Polymer films are preferred because they can be made with greater thickness and thus the ability to sorb a larger quantity of analyte vapor, which induces a stronger sensor response.

The location and thickness of polymer coatings have been shown to greatly influence sensor response. See, for example, Wright, Y. J. et al., Study of a microcapillary pipette-assisted method to prepare polyethylene glycol-coated microcantilever sensors. *Sensors and Actuators B-Chemical* 2005, 107 (1), 242-251; Thundat, T. et al., Detection of Mercury-Vapor Using Resonating Microcantilevers. *Applied Physics Letters* 1995, 66 (13), 1695-1697; and Chen, G. Y. et al., Adsorption-induced surface stress and its effects on resonance frequency of microcantilevers. *Journal of Applied Physics* 1995, 77 (8), 3618-3622.

Polymer film deposition methods on NEMS sensors heretofore have been limited to the dropcasting or spincoating of dilute polymer solutions that coat the entire substrate with a thin polymer film. The maximum film thickness achievable by these methods is approximately 10 nm, which limits dynamic range in terms of both minimum and maximum detectable levels. Attempts to form thicker films have resulted in NEMS cantilevers that are glued to the underlying substrate and thereby rendered unable to resonate. In addition, with these methods, film homogeneity is difficult or impossible to control, leading to variation in film thickness between adjacent sensors and across the surface of a single sensor. Such variation in thickness decreases the reproducibility of sensor performance. In addition, for applications demanding detection of a target vapor from a very small total sample volume, analyte sorption onto non-sensitive surfaces such as the underlying substrate decreases the number of molecules available for detection via sorption onto NEMS, which limits sensitivity.

Previously, dropcasting or dropcoating dilute polymer solutions was necessary to coat nanocantilevers with thin polymer films. FIG. 1A and FIG. 1B show the limitations on film thickness imposed by these methods.

Inkjet printing, which has been used to deposit polymer films on single microscale cantilevers produces solution droplet on the order of tens of microns. See for example Bietsch, A. et al., Rapid functionalization of cantilever array sensors by inkjet printing. *Nanotechnology* 2004, 15 (8), 873-880. Microcapillary pipettes have also been used, but suffer from the same droplet size problem. See Wright, 2005. Dip pen lithography is capable of the precision to deposit polymer films on single nanocantilevers, but is a serial process and coating of thousands of sensors would be too time intense to be industrially viable. See for example, Salaita, K. et al., Applications of dip-pen nanolithography. *Nat. Nanotechnol.* 2007, 2 (3), 145-155.

There is a need for systems and methods to deposit films on nanocantilevers that overcome the above recited limitations.

SUMMARY OF THE INVENTION

According to one aspect, the invention features a cantilever chemical vapor sensor, comprising a cantilever structure having a base, having at least one leg extending from the base and having a tip at a distal end of the at least one leg, the cantilever structure attached to a substrate at the base thereof and configured to oscillate at a natural resonant frequency $F_0$; a sorbent film attached to a location of the cantilever structure selected from the group of locations consisting of the base, the at least one leg and the tip, and absent from another of the locations of the cantilever structure selected from the group of locations consisting of the base, the at least one leg and the tip, the sorbent film configured to collect by sorbtion molecules from a vapor is contact with the cantilever structure, the molecules collected configured to cause a change $\Delta F$ in the natural resonant frequency $F_0$; and a signal output port configured to provide a signal representative of the oscillation frequency of the cantilever structure.

In one embodiment, a promoter film is situated on a surface of the cantilever structure at the location of the cantilever structure selected from the group of locations consisting of the base, the at least one leg and the tip where the sorbent film is attached.

In another embodiment, the promoter film is a layer of gold.

In yet another embodiment, a polymerization initiator is present on the layer of gold.

In still another embodiment, another of the locations of the cantilever structure selected from the group of locations consisting of the base, the at least one leg and the tip where the sorbent film is absent is a location where a passivation layer is present.

In a further embodiment, the passivation layer comprises chromium.

In yet a further embodiment, the passivation layer comprises oxidized chromium having a self assembled monolayer deposited on the oxidized chromium.

In an additional embodiment, the cantilever chemical vapor sensor further comprises a promoter film and a passivation layer, the promoter film applied to at least two of the locations of the cantilever structure selected from the group of locations consisting of the base, the at least one leg and the tip, and the passivation layer applied over the promoter layer at at least one of the locations of the cantilever structure selected from the group of locations consisting of the base, the at least one leg and the tip.

In still a further embodiment, the sorbent film is a polymer having a glass temperature Tg.

According to another aspect, the invention relates to a method of fabricating a cantilever chemical vapor sensor. The method comprises the steps of defining on a surface of a substrate a plurality of regions to be fabricated into a cantilever structure, which cantilever structure when completed comprises a base, at least one leg extending from the base and a tip at a distal end of the at least one leg, and a signal output port configured to provide a signal representative of an oscillation frequency of the cantilever structure; applying and patterning a promoter layer at one or more of the regions defined as the base, the at least one leg and the tip; overcoating the promoter layer with a passivating layer at at least one of the regions defined as the base, the at least one leg and the tip, while leaving a portion of the promoter layer uncoated; etching the substrate so as to fabricate the cantilever structure comprising the base, the at least one leg extending from the base and the tip at a distal end of the at least one leg, the base of the cantilever structure remaining attached to the substrate and the signal output port; and depositing a sorbing layer over the uncoated promoter layer while inhibiting the sorbing layer from depositing on the passivating layer; the cantilever structure configured to oscillate at a natural resonant frequency $F_O$ in the absence of a sorbate on the sorbing layer and to oscillate at a frequency $F_O+\Delta F$ in the presence of a sorbate on the sorbing layer.

In one embodiment, the promoter layer comprises gold. In another embodiment, the method further comprises the step of overcoating the gold with a polymerization initiator prior to the step of depositing a sorbing layer over the uncoated promoter layer.

In yet another embodiment, the passivating layer comprises chromium with a native oxide.

In still another embodiment, the method further comprises the steps of oxidizing the chromium and forming a self assembled monolayer of an additional passivating layer on the oxidized chromium prior to the step of depositing a sorbing layer over the uncoated promoter layer.

In a further embodiment, the step of applying and patterning a promoter layer comprises the steps of depositing a gold layer; and patterning the gold layer.

In yet a further embodiment, the method further comprises the step of applying a polymerization initiator to the patterned gold layer to provide a self assembled monolayer of a substance that promotes deposition of the adsorbing layer at that location.

In an additional embodiment, the step of overcoating the promoter layer with a passivating layer comprises the steps of depositing a chromium layer on a region where deposition of the sorbing layer is to be inhibited; and patterning the chromium layer.

In one more embodiment, the method further comprises the steps of oxidizing the chromium layer to provide an oxidized chromium surface; and depositing a self assembled monolayer of a substance that further passivates the oxidized chromium surface to prevent attachment of polymer initiator to that surface.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

DETAILED DESCRIPTION

We describe methods useful to deposit polymer films of improved (greater) thickness and homogeneity, while also localizing the film to a chosen nanoscale area on a nanocantilever sensor. See FIG. 2A through FIG. 2D.

Figure 1A:
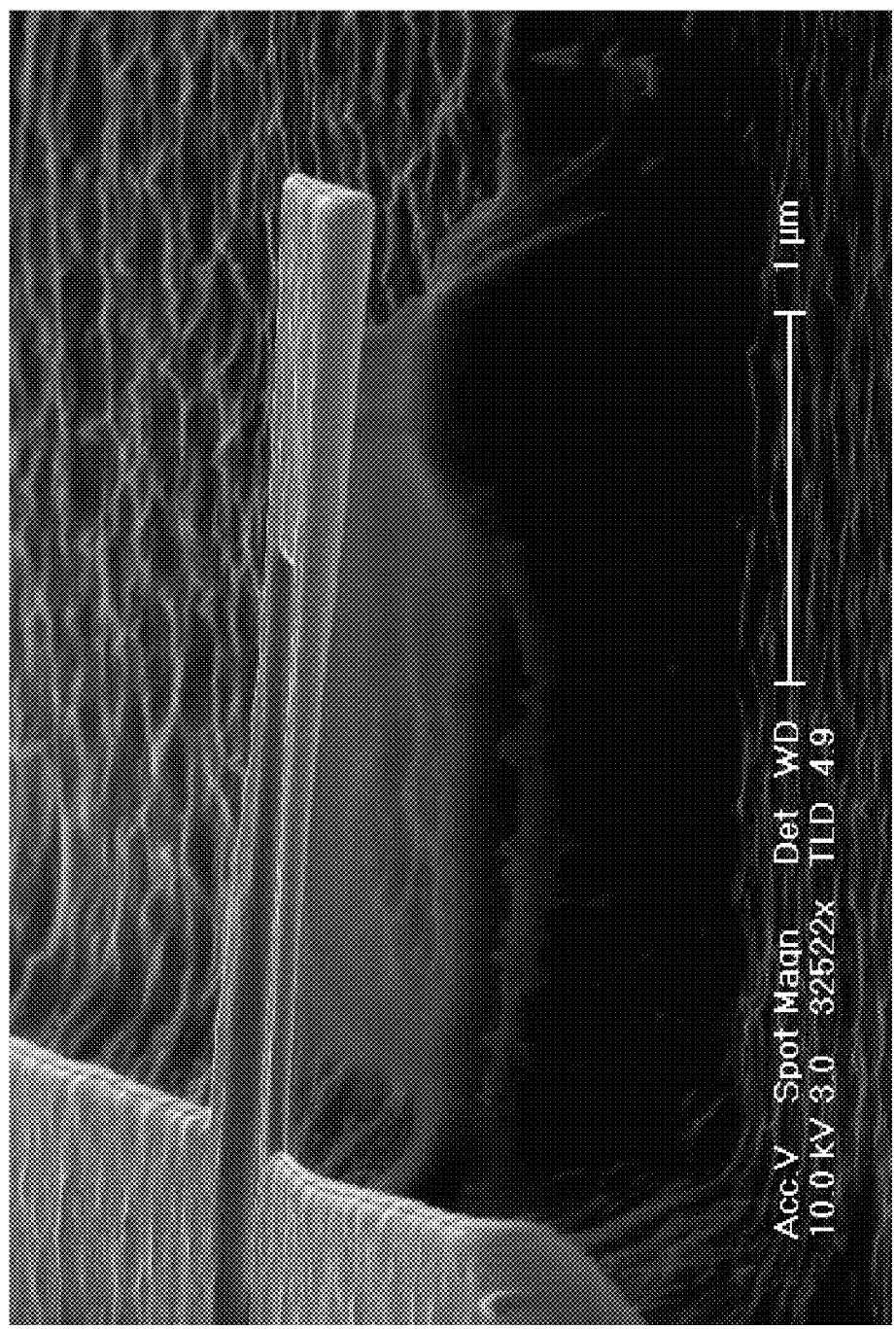
FIG. 1A is an image of a prior art dropcast PMMA film on a nanocantilever in which the cantilever became glued to the substrate when a 60 nm thick film was cast.
Figure 1B:
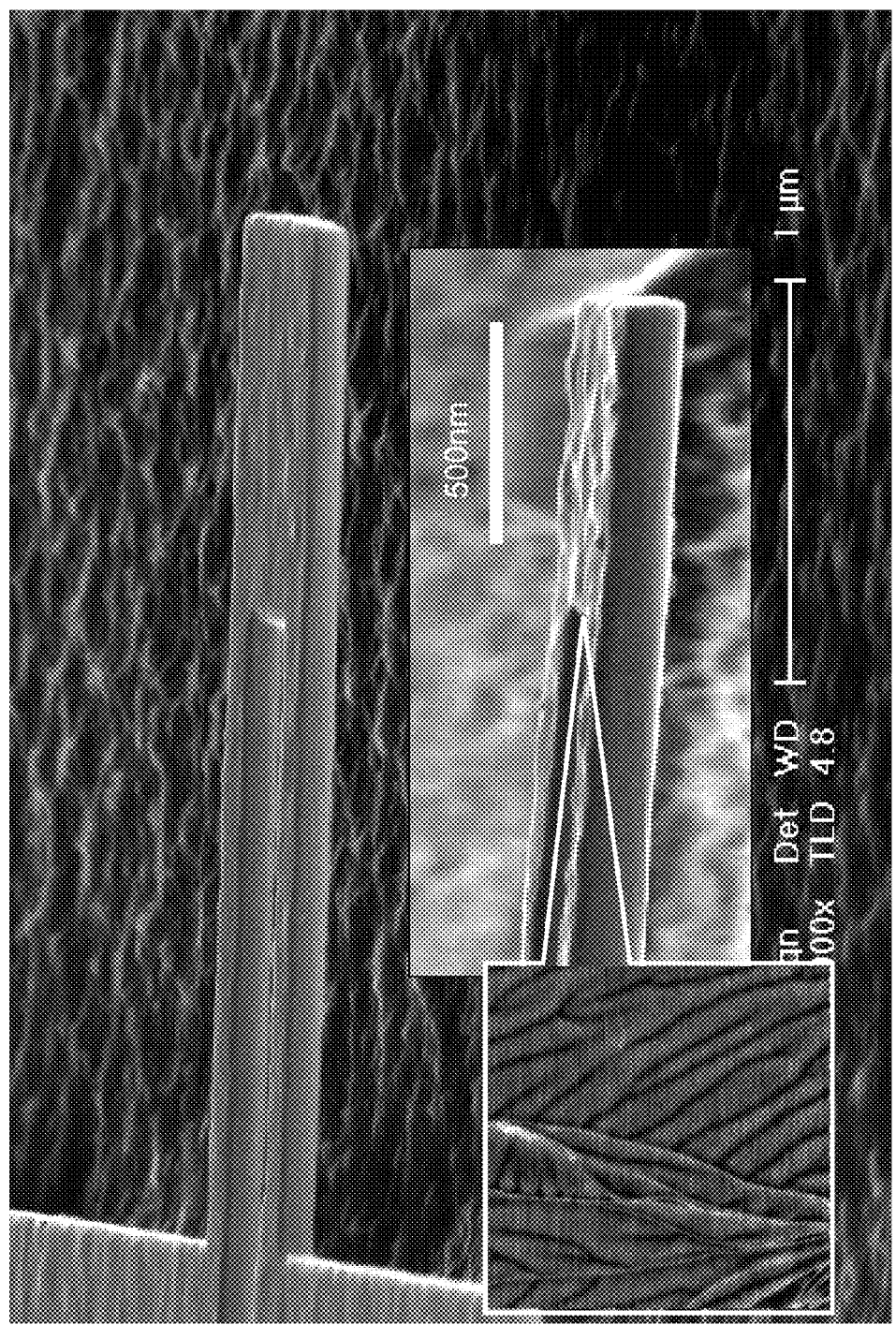
FIG. 1B is an image of a prior art dropcast PMMA film on a nanocantilever showing a successful 10 nm thick PMMA film. The inset is an atomic force microscopy (AFM) image showing the polymer film surface morphology.
Figure 2A:
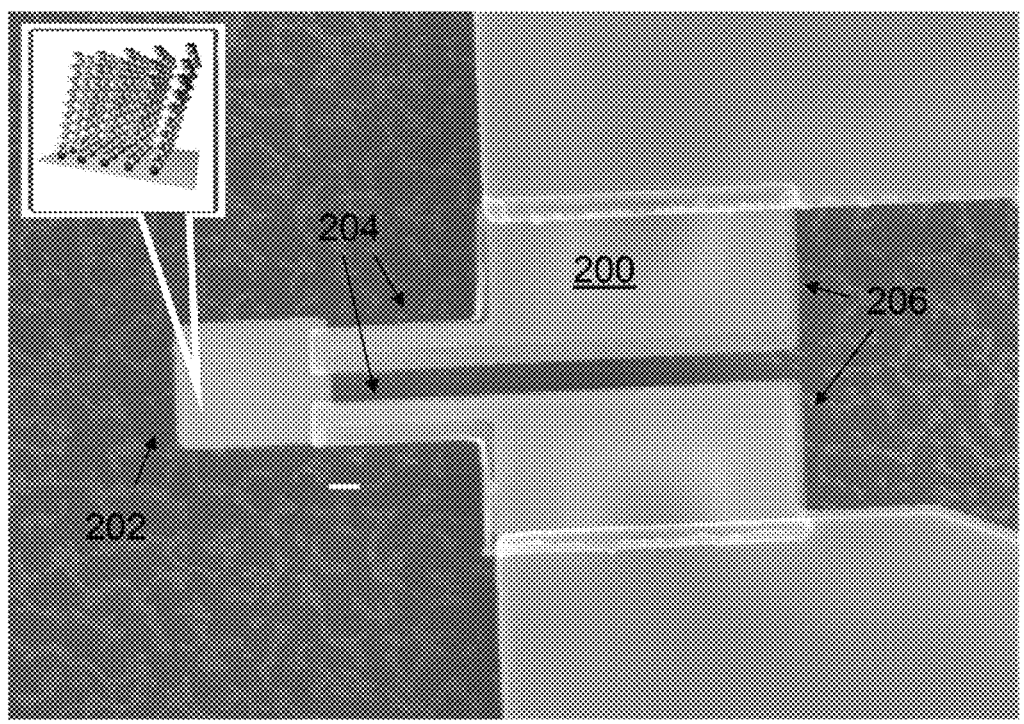
FIG. 2A is a contrast-enhanced top-down SEM image of a chromium masked cantilever.

FIG. 2A is a contrast-enhanced top-down SEM image of a chromium masked cantilever 200. The cantilever includes a cantilever tip 202, cantilever legs 204 and cantilever bases 206. The bases 206 are clamped to the silicon wafer from which the NEMS cantilever structure is produced by lithography and etching. The white bar in the image represents a distance of 200 nm. The inset illustrates in schematic form a self assembled monolayer grown in a specific location on the cantilever.

Figures 2B, 2C, 2D:
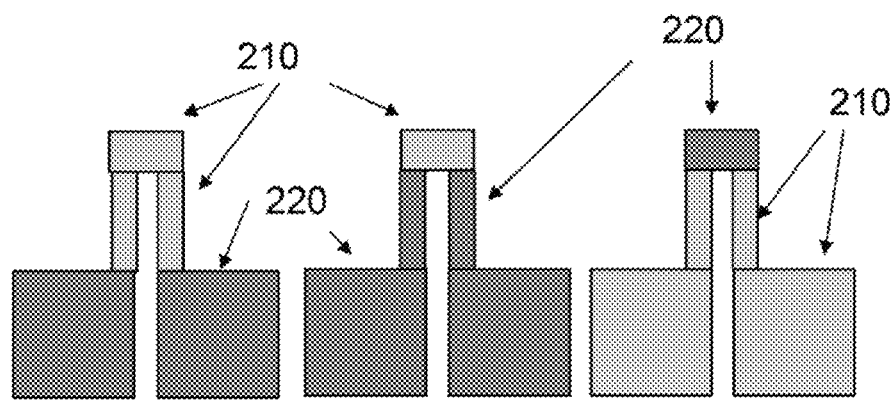
FIG. 2B, FIG. 2C and FIG. 2D are images showing the three geometries fabricated to explore the effect of localizing polymer coating.

Three different geometries have been fabricated to determine the optimal region for polymer coating for different operational environments and polymer/analyte pairs. FIG. 2B, FIG. 2C and FIG. 2D are images showing the three geometries fabricated to explore the effect of localizing polymer coating. Gold layer 210 is deposited on the cantilever tip 202 and the cantilever legs 204 in FIG. 2B, on the tip 202 in FIG. 2C, and on the legs 204 and bases 206 in FIG. 2D. The remainder of each cantilever is coated with a chromium layer 220, as indicated in the drawings. In this way, deposition of polymer film layers can be localized to specific regions of a cantilever structure.

We have demonstrated the ability to localize a thicker, smoother polymer film to only the NEMS nanocantilever sensor, leaving the substrate bare. Additionally, further localizing the polymer film to either the tip or clamped end of a nanocantilever directs vapor sorption to maximize mass loading or stiffening, which provides improved device sensitivity because the two response mechanisms (loading and stiffening) can be controlled to oppose each other in terms the direction of resonant frequency shift.

The invention provides a method to grow a localized polymer film on a nanoelectromechanical system (NEMS) resonator chemical vapor sensor. Sections of the resonator where polymer growth is to be inhibited are masked with chromium and passivated with a self assembled monolayer. Surface initiated atom transfer polymerization (SI-ATRP) is then used to grow a polymer film that is localized to the exposed gold areas of the NEMS resonator. The ability to deposit thicker polymer films can provide systems having enhanced sensitivity. Localization of the polymer film to the tip of clamped end provides the ability to control the shifts in the response pattern of a sensor.

The glass transition temperature (Tg) of a polymer marks a phase transition above which the polymer chains are capable of motion, making the material "rubbery." Below Tg, the polymer chains are locked into a single configuration, rendering the material stiff and "glassy." Whether a polymer exists above or below its Tg affects nanocantilever response. The diffusion of vapor molecules into a polymer is much faster above the polymer's Tg. A polymer with a Tg below the operating temperature of the nanocantilever sensor will have less effect on the nanocantilever's stiffness, such that when vapor diffuses into the film and causes it to swell, it will induce little or no strain on the sensor. By choosing a polymer with a high or low Tg, the observed sensor response with respect to temperature can be controlled. One high glass transition temperature polymer and two low glass transition temperature polymers have been polymerized on the nanocantilever sensors.

Fabrication

The top surface of the NEMS resonator is coated with a 20 nm thick gold film, sections of which are masked to inhibit polymer growth. After patterning the mask area with electron beam lithography, a thin film of chromium of a similar thickness is deposited by thermal evaporation on regions of the device where polymer film growth is to be suppressed or inhibited. Electron beam lithography is used to pattern the chromium masking layer on top of the gold layer before the cantilevers are suspended using a plasma etch. In a preferred embodiment, the chromium is coated with a layer of native oxide. A self assembled monolayer (SAM) of n-hexylphosphonic acid is used to further passivate the oxidized chromium surface to prevent attachment of polymer initiator molecules to that surface.

Localization of polymer coating is achieved utilizing a combination of SI-ATRP and disulfide SAM formation on gold. The polymerization initiator (available from ATRP Solutions, Inc., PO Box 19386, Pittsburgh, Pa. 15213) contains a disulfide which will adhere to the gold surface, and polymerization only occurs (or very preferentially occurs) at those locations. Surface initiated atom transfer polymerization (SI-ATRP) is then used to grow a polymer film which is localized to the bare gold surface.

Figure 3A:
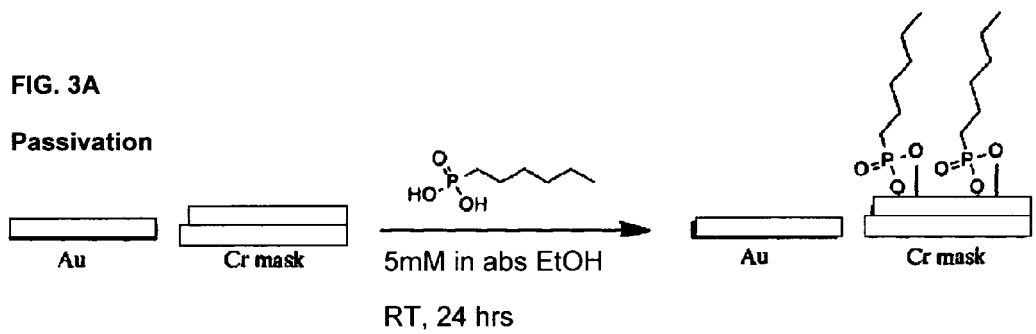
FIG. 3A is a diagram that illustrates the chromium passivation step of a reaction scheme used to grow localized polymer films.

FIG. 3A is a diagram that illustrates the chromium passivation step of a reaction scheme used to grow localized polymer films.

Figure 3B:
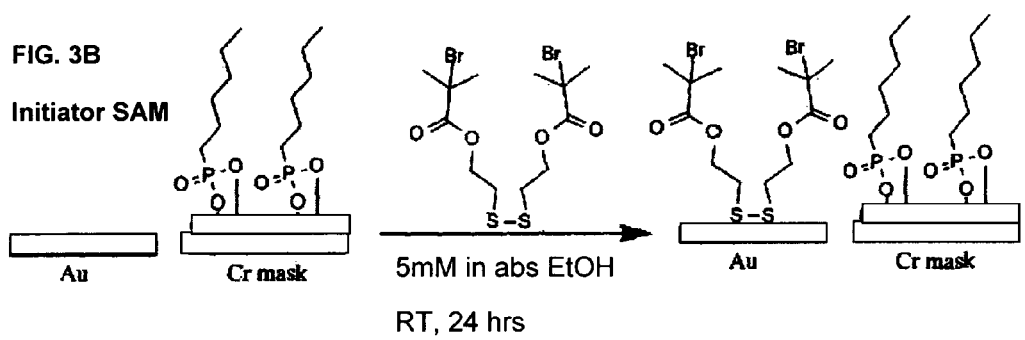
FIG. 3B is a diagram that illustrates the self assembly step of the initiator on a gold layer, but not on the passivated chromium layer, in the reaction scheme used to grow localized polymer films.

FIG. 3B is a diagram that illustrates the self assembly step of the initiator on a gold layer, but not on the passivated chromium layer, in the reaction scheme used to grow localized polymer films.

Figure 3C:
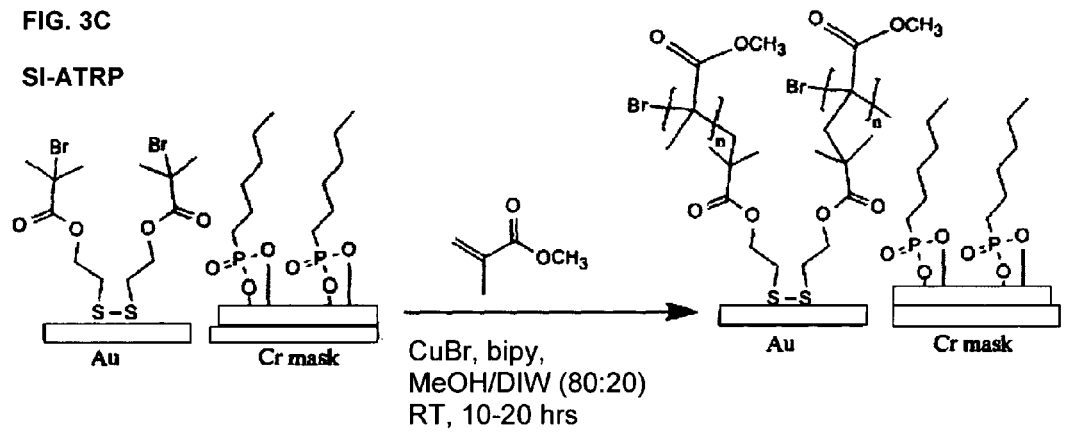
FIG. 3C is a diagram that illustrates the step of SI-ATRP to form a polymer film only on the gold in the reaction scheme used to grow localized polymer films.

FIG. 3C is a diagram that illustrates the step of SI-ATRP to form a polymer film only on the gold in the reaction scheme used to grow localized polymer films.

ATRP is amenable to polymerization of many different monomers including those which can be modified post polymerization to incorporate functional groups incompatible with ATRP.

We now give as examples results for poly(methyl methacrylate) (PMMA), poly(methyl acrylate) (PMA), and poly (n-butyl methacrylate) (PBMA) that have been polymerized on nanocantilevers. Table I gives the name, the formula for the repeat unit, and Tg for each of the polymers.

TABLE I

| Material | Repeat unit | Tg |
| --- | --- | --- |
| Poly(methyl acrylate) | —[CH$_2$—CH]—<br>\|<br>C=O<br>\|<br>O<br>\|<br>CH$_3$ | 9 °C. |
| Poly(n-butyl methacrylate) | CH$_3$<br>\|<br>—[CH$_2$—C]—<br>\|<br>C=O<br>\|<br>O<br>\|<br>(CH$_2$)$_3$<br>\|<br>CH$_3$ | 20 °C. |
| Poly(methyl methacrylate) | CH$_3$<br>\|<br>—[CH$_2$—C]—<br>\|<br>C=O<br>\|<br>O<br>\|<br>CH$_3$ | ca. 105 °C. |

Preparative Methods

In order to achieve localized polymer coating of nanoscale devices, we have adopted a bottom up strategy based on surface initiated atom transfer radical polymerization (SI-ATRP), a technique which enables the growth of a polymer film directly from a surface. See Barbey, R. et al., Polymer Brushes via Surface-Initiated Controlled Radical Polymerization: Synthesis, Characterization, Properties, and Applications. *Chemical Reviews* 2009, 109 (11), 5437-5527. SI-ATRP has been used to grow polymer films on static microscale cantilevers for various sensing applications in liquid and vapor environments. See for example, Bumbu, G. G. et al., Synthesis and characterization of polymer brushes on micromechanical cantilevers. *Macromol. Chem. Phys.* 2004, 205 (13), 1713-1720; Bumbu, G. G. et al., Micromechanical cantilever technique: A tool for investigating the swelling of polymer brushes. *Langmuir* 2007, 23 (4), 2203-2207; and Bradley, C. et al., Response Characteristics of Thermoresponsive Polymers Using Nanomechanical Cantilever Sensors. *Macromol. Chem. Phys.* 2009, 210 (16), 1339-1345. We are unaware of any effort that has been made to localize the coating onto specific sections of a single sensor, prior to this work.

ATRP is a controlled or living polymerization method that results in polymer chains with a low polydispersity index (PDI), indicating a small distribution of chain lengths. When ATRP is initiated from a surface (SI-ATRP), in a process in which polymer chains grow directly off of the substrate, a film of uniform thickness is the result. Since NEMS sensor responses are sensitive to the location at which vapor sorption occurs, film thickness uniformity is advantageous to achieve reproducible results.

Methyl Methacrylate

Poly(methyl methacrylate) (PMMA, also known as Plexiglas, Lucite, and Perspex) is a high Tg polymer. Tg=105° C. for atactic PMMA. The SI-ATRP of methyl methacrylate (MMA) on nanocantilevers was performed accordingly to the procedure published by Jones and Huck (Jones, D. M.; Huck, W. T. S., Controlled surface-initiated polymerizations in aqueous media. *Adv. Mater.* 2001, 13 (16), 1256-1259).

A new passivation step was added to prevent the initiator from sticking to the oxidized chromium mask. Substrates were cleaned with hexane, acetone, THF, methanol, and absolute methanol, followed by an 8 minute UV/ozone plasma clean and 18 MΩ cm$^{-1}$ deionized water (DIW) rinse. Substrates were then immediately passivated with n-hexylphosphonic acid to ensure good coverage of the oxidized chromium surface. Passivation with n-hexylphosphonic acid was done as a simple self assembly by soaking the flat substrate or chip with suspended nanocantilevers in a 5 mM ethanolic solution of the acid for 24 hours. The initiator self assembly proceeds in a similar fashion with care being taken to keep the solutions in the dark to prevent possible degradation by UV light.

This polymerization is air sensitive. Solvents and monomer were purged with nitrogen prior to addition of the catalyst. The details were unchanged from the reaction reported in the Jones and Huck paper. For a typical reaction a two-necked roundbottom flask equipped with a stirbar was charged with methyl methacrylate (15 g), methanol (12 mL), and deionized water (3 mL). The flask was sealed with septa and pierced with needles for nitrogen purging. To purge the reaction solution, nitrogen was bubbled while sonicating for 15 min and then an additional 30 min with only stirring. At this point the catalyst, copper (I) bromide (228 mg, 1.59 mmol) and 2,2'-bypyridine (516 mg, 3.30 mmol) was quickly added and the septa replaced. Nitrogen purging was continued and the flask was sonicated or stirred until the catalyst was dissolved, giving a homogenous dark brown solution.

For the polymerization reaction substrates were suspended in scint vials equipped with magnetic stir bars and septa, and were continuously purged with nitrogen. A syringe was used to transfer the reaction solution to the vials to prevent contact with oxygen, and the polymerization was carried out for the desired time, usually 15-20 hrs. The solution was exposed to air to stop the polymerization. Substrates were rinsed with methanol, DIW, THF, and absolute ethanol. Because this polymerization does not require the use of sacrificial initator in the bulk solution, polymerization only occurs at surface bound initiator molecules, making rinsing simple.

A maximum film thickness 90 nm of PMMA was achieved after approximately 20 hrs of polymerization. The PMMA deposited preferentially on gold as compared to chromium or silicon. The film thickness ratio of PMMA on gold to chromium is 20:1 in favor of gold, and approximately 40:1 for gold relative to silicon. These ratios are independent of polymerization time.

Methyl Acrylate

Polymerization of poly(methyl acrylate) (PMA) was adapted from work on SI-ATRP of PMA on silicon. See Matyjaszewski et al., Polymers at interfaces: Using atom transfer radical polymerization in the controlled growth of homopolymers and block copolymers from silicon surfaces in the absence of untethered sacrificial initiator. *Macromolecules* 1999, 32 (26), 8716-8724. PMA has a Tg of 9° C.

Figure 15:
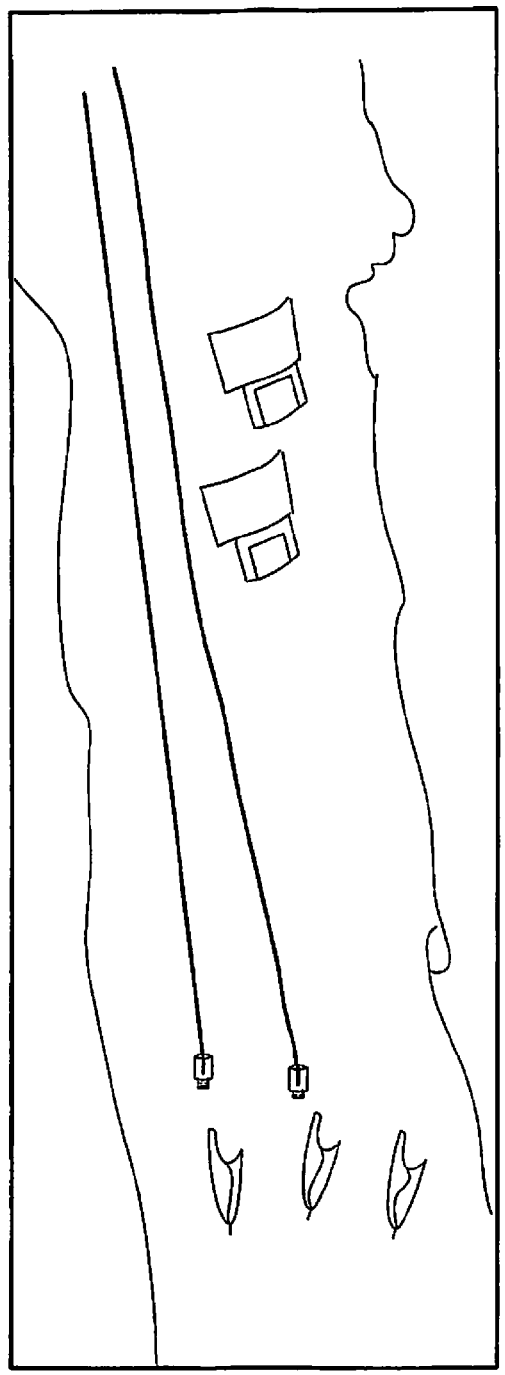
FIG. 15 is an image of clips attached to supporting needles that can be used in fabricating coatings according to the principles of the invention. Substrates were suspended in the reaction test tube with flat clips wired to long needles. The needle was pierced through a septum, which was then used to seal the test tube. The pointed tip of the needle was wrapped in parafilm to seal it and to prevent accidental injury.

The synthesis was adapted to a lower reaction temperature as the original synthesis for growing polymers from silicon surfaces utilized a more thermally stable silane bonded initiator. Methyl acrylate (MA) was first passed through an inhibitor removal column. A two necked round bottom flask was charged with the purified MA (20 g) and N,N,N',N'',N''-pentamethyldiethylenetriamine (PMDETA) (420 mg), and was then sealed with septa. The flask was then sonicated while the solution was sparged with argon for 45 min. A large test tube fitted with a magnetic stir bar was charged with copper (I) bromide (CuBr) (257 mg) and copper (II) bromide (CuBr$_2$) (15 mg). The substrate (flat or cantilevers) was suspended in the test tube with a flat clip that was wired to a metal needle. The needle was pierced through the septum which was then used to seal the test tube, allowing the substrate height to be controlled (see FIG. 15). The pointed tip of the needle was wrapped in parafilm to seal it and to prevent accidental injury. Substrate suspension allowed the solution to be stirred without damaging the substrate. The tube was purged continuously with argon. The test tube was maintained at 50° C. by emersion in an oil bath for the duration of the reaction. The sparged solution was transferred to the test tube using a syringe. Care was taken to prevent solution from contacting the substrate, which was kept suspended above the liquid. After stirring 1 hr all CuBr had dissolved, but some CuBr$_2$ solids remained. The substrate was lowered into the reaction solution. The reaction was allowed to proceed for up to 48 hrs, which resulted in a 100 nm thick PMA film. All CuBr$_2$ was dissolved after approximately 1 hr after the polymerization reaction had commenced. The solution was exposed to air to stop the polymerization. Substrates were rinsed with chloroform, methanol, and absolute ethanol.

Poly(n-butyl methacrylate)

Polymerization of poly(n-butyl methacrylate) (PBMA) was performed at room temperature using water-accelerated SI-ATRP, according to work by Xu, et al. (Xu, C.; Wu, T.; Drain, C. M.; Batteas, J. D.; Fasolka, M. J.; Beers, K. L., Effect of block length on solvent response of block copolymer brushes: Combinatorial study with block copolymer brush gradients. *Macromolecules* 2006, 39 (9), 3359-3364.)

For a typical reaction a two-necked round bottom flask was charged with n-butyl methacrylate (10 mL) (purified by passing through an inhibitor removal column immediately prior to the reaction), isopropanol (9 mL), and water (18 MΩ/cm) (1 mL). The flask was sealed with septa and pierced with needles to deliver and release an inert gas. The solution was sparged with argon while sonicating for 45 min to remove oxygen. At this point the catalyst, copper (I) bromide (38 mg) and 2,2'-bypyridine (98 mg), was quickly added and the septa replaced. Sparging with argon was continued, and the flask was sonicated until catalyst is dissolved (approximately 30 min), giving a homogonous dark brown solution.

For the polymerization reaction, substrates were suspended in scint vials equipped with magnetic stir bars and septa. The vials were continuously purged with argon. A syringe was used to transfer the reaction solution to the vials to prevent contact with oxygen, and the polymerization was carried out at room temperature for the desired time. The solution was exposed to air to stop the polymerization. Substrates were rinsed with methanol, deionized water (DIW), THF, and absolute ethanol. A 12 hr reaction resulted in the growth of a 100 nm thick PBMA film on the substrate, as measured by ellipsometry and scanning electron microscopy (SEM).

Figure 4:
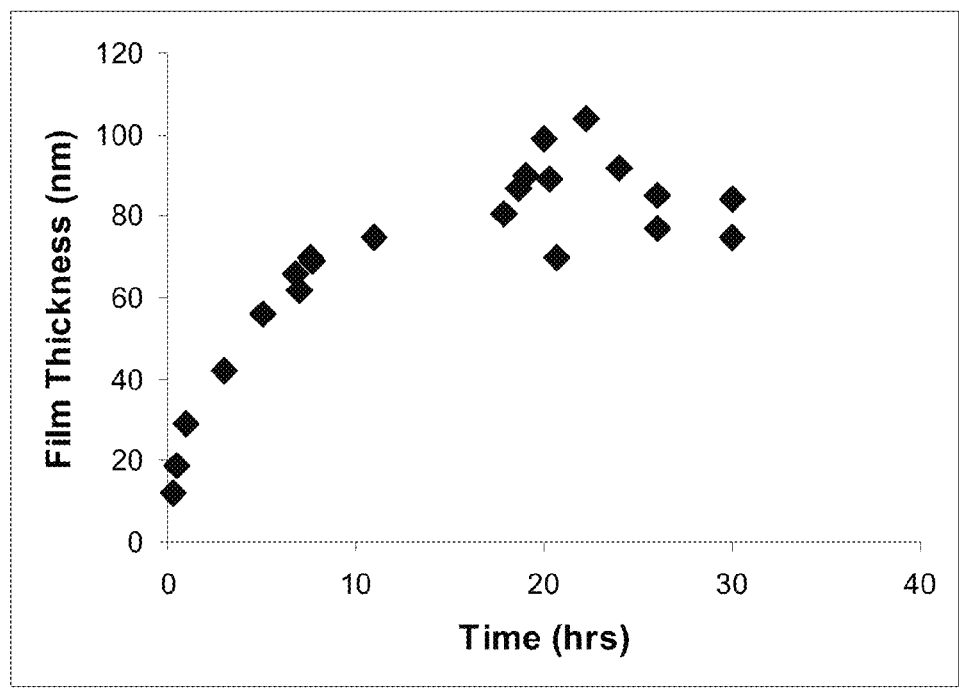
FIG. 4 is a graph of PMMA film thickness on flat gold substrates as measured by ellipsometry as a function of polymerization time.

To verify the selectivity of this scheme, polymer film thicknesses on flat substrates of silicon with native oxide, as well as silicon with 30 nm thick films of gold and chromium has been measured with ellipsometry. After a 20 hr polymerization, a 90 nm thick PMMA film on gold, a 6 nm on chromium, and a 3 nm on silicon are typically observed. SEM images of both gold only cantilevers and cantilevers with chromium masked regions also show growth of a thick PMMA film localized to the gold surface. FIG. 4 is a graph of PMMA film thickness on flat gold substrates as measured by ellipsometry as a function of polymerization time.

Figure 5A:
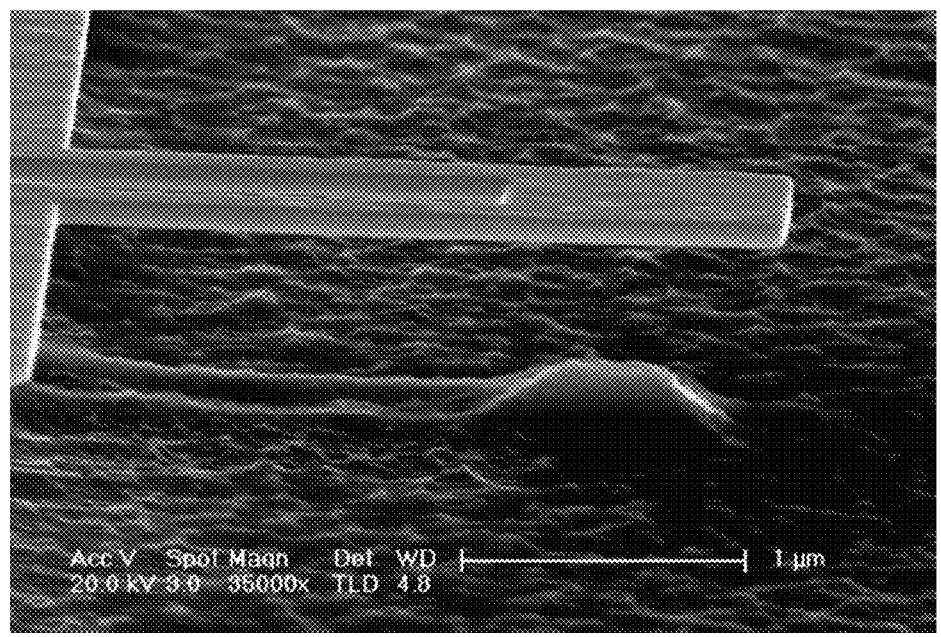
FIG. 5A is a contrast-enhanced SEM image of a nanocantilever having only a gold coating, on which a 5-10 nm dropcast polycaprolactone film was deposited.

FIG. 5A is a contrast-enhanced SEM image of a nanocantilever having only a gold coating, on which a 5-10 nm dropcast polycaprolactone film was deposited.

Figure 5B:
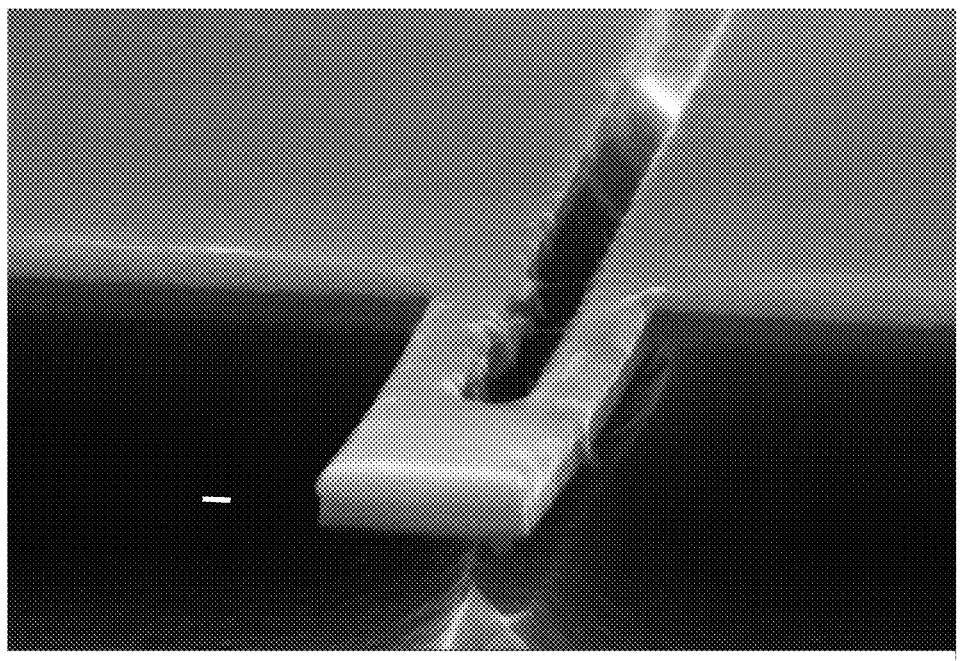
FIG. 5B is a contrast-enhanced SEM image of a nanocantilever having only a gold coating, on which a 80-90 nm SI-ATRP PMMA film was deposited. The white bar in the image represents a distance of 100 nm.

FIG. 5B is a contrast-enhanced SEM image of a nano cantilever having only a gold coating, on which a 80-90 nm SI-ATRP PMMA film was deposited. The white bar in the image represents a distance of 100 nm.

Figure 5C:
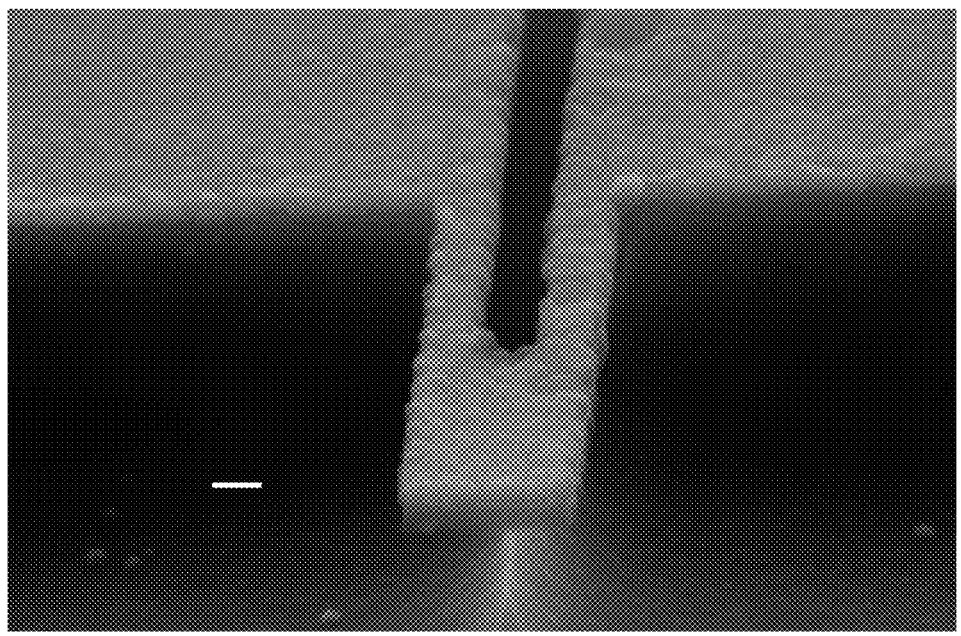
FIG. 5C is a contrast-enhanced SEM image of a nanocantilever coated with PMA polymer film grown via SI-ATRP. The white bar in the image represents a distance of 200 nm.

FIG. 5C is a contrast-enhanced SEM image of a nanocantilever coated with PMA polymer film grown via SI-ATRP. The white bar in the image represents a distance of 200 nm.

Figure 5D:
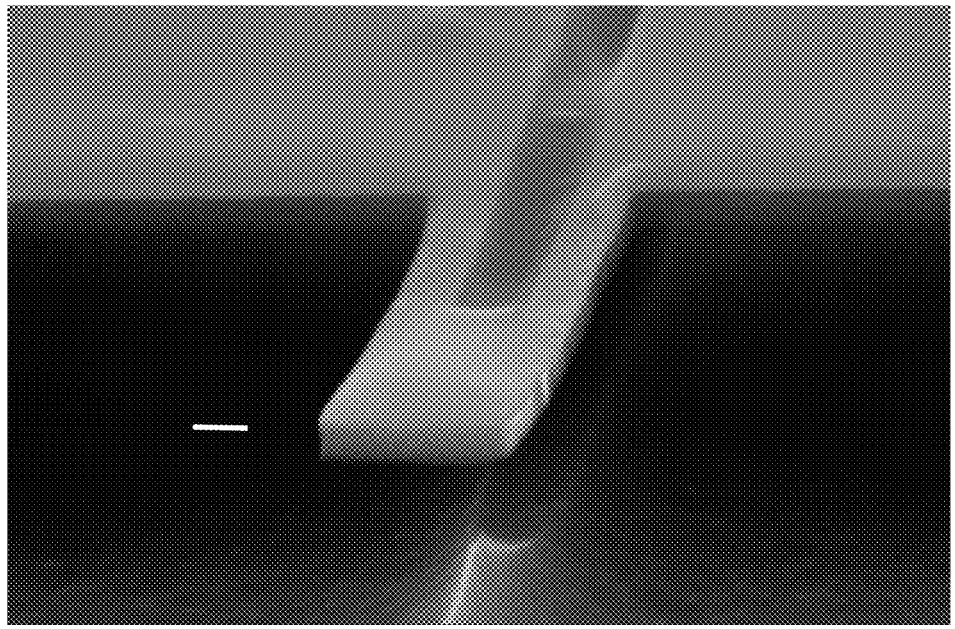
FIG. 5D is a contrast-enhanced SEM image of a nanocantilever coated with PBMA polymer film grown via SI-ATRP. PBMA coated cantilevers used as vapor sensors all showed polymer growth between cantilever legs. The white bar in the image represents a distance of 200 nm.

FIG. 5D is a contrast-enhanced SEM image of a nanocantilever coated with PBMA polymer film grown via SI-ATRP. PBMA coated cantilevers used as vapor sensors all showed polymer growth between cantilever legs. The white bar in the image represents a distance of 200 nm.

Figure 6A:
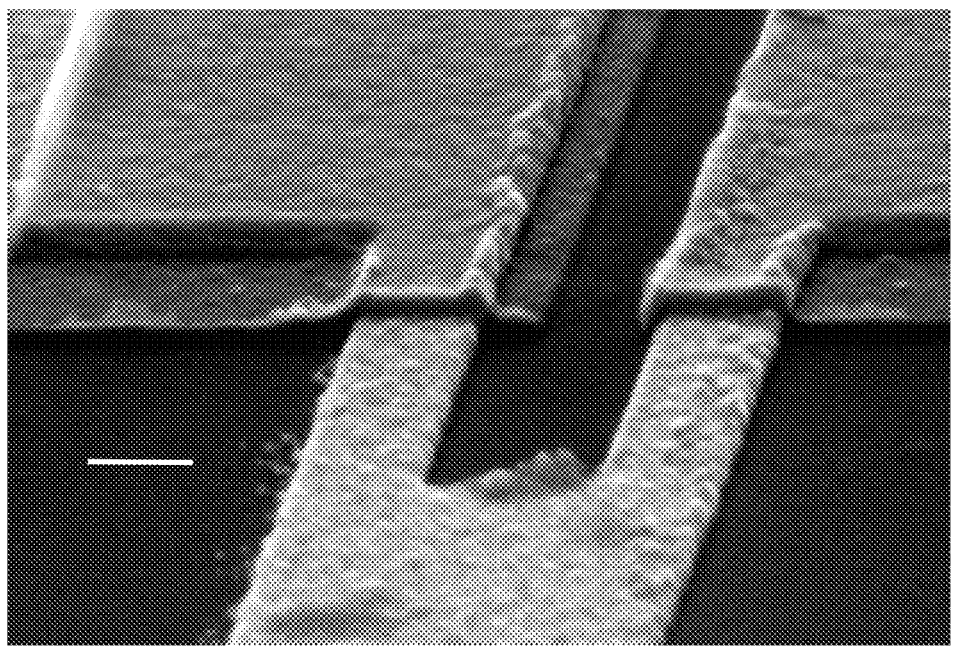
FIG. 6A is a contrast-enhanced SEM image of an uncoated nanocantilever. The white bar in the image represents a distance of 200 nm.

FIG. 6A is a contrast-enhanced SEM image of an uncoated nanocantilever. The white bar in the image represents a distance of 200 nm.

Figure 6B:
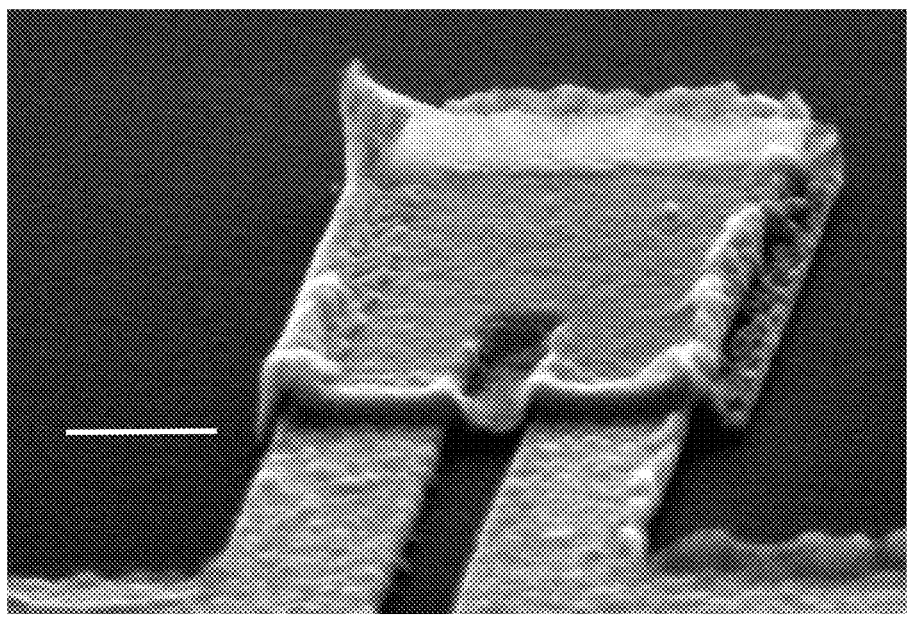
FIG. 6B is a contrast-enhanced SEM image of an uncoated nanocantilever. The white bar in the image represents a distance of 300 nm.

FIG. 6B is a contrast-enhanced SEM image of an uncoated nanocantilever. The white bar in the image represents a distance of 300 nm.

Figure 6C:
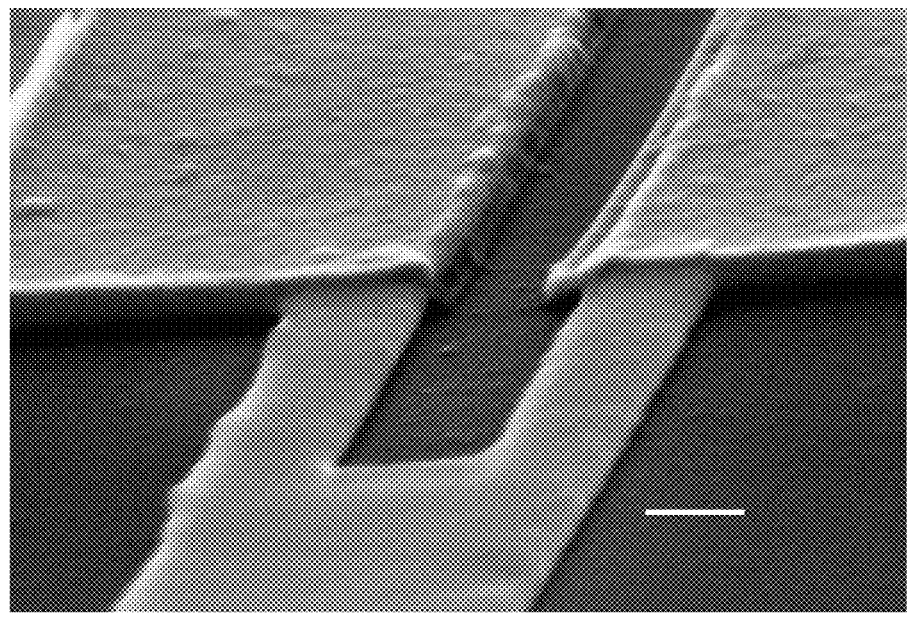
FIG. 6C is a contrast-enhanced SEM image of a nanocantilever after SI-ATRP coating of PMMA. The white bar in the image represents a distance of 200 nm.

FIG. 6C is a contrast-enhanced SEM image of a nanocantilever after SI-ATRP coating of PMMA. The white bar in the image represents a distance of 200 nm.

Figure 6D:
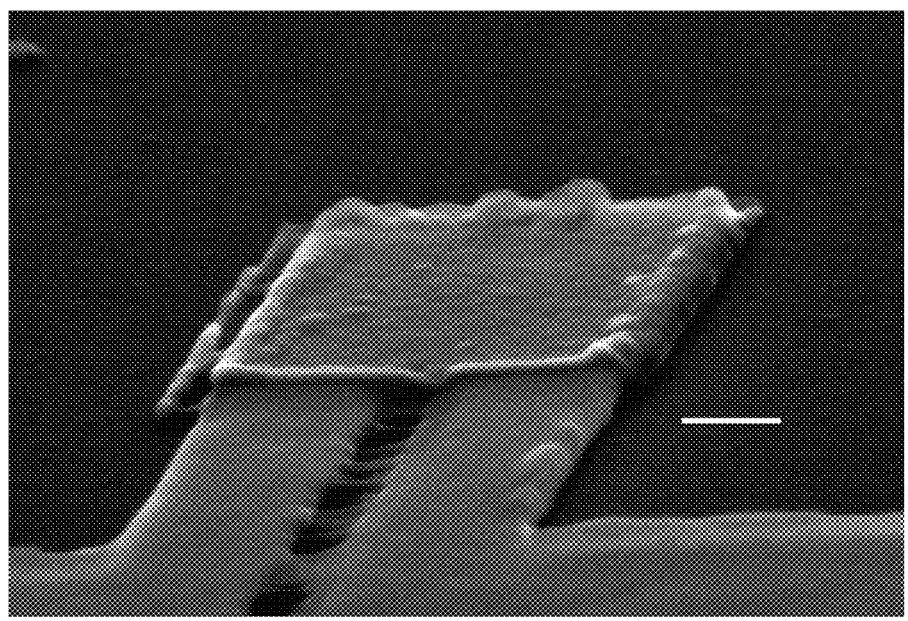
FIG. 6D is a contrast-enhanced SEM image of another portion of a nanocantilever after SI-ATRP coating of PMMA. The white bar in the image represents a distance of 200 nm.

FIG. 6D is a contrast-enhanced SEM image of another portion of a nanocantilever after SI-ATRP coating of PMMA. The white bar in the image represents a distance of 200 nm.

Figure 7:
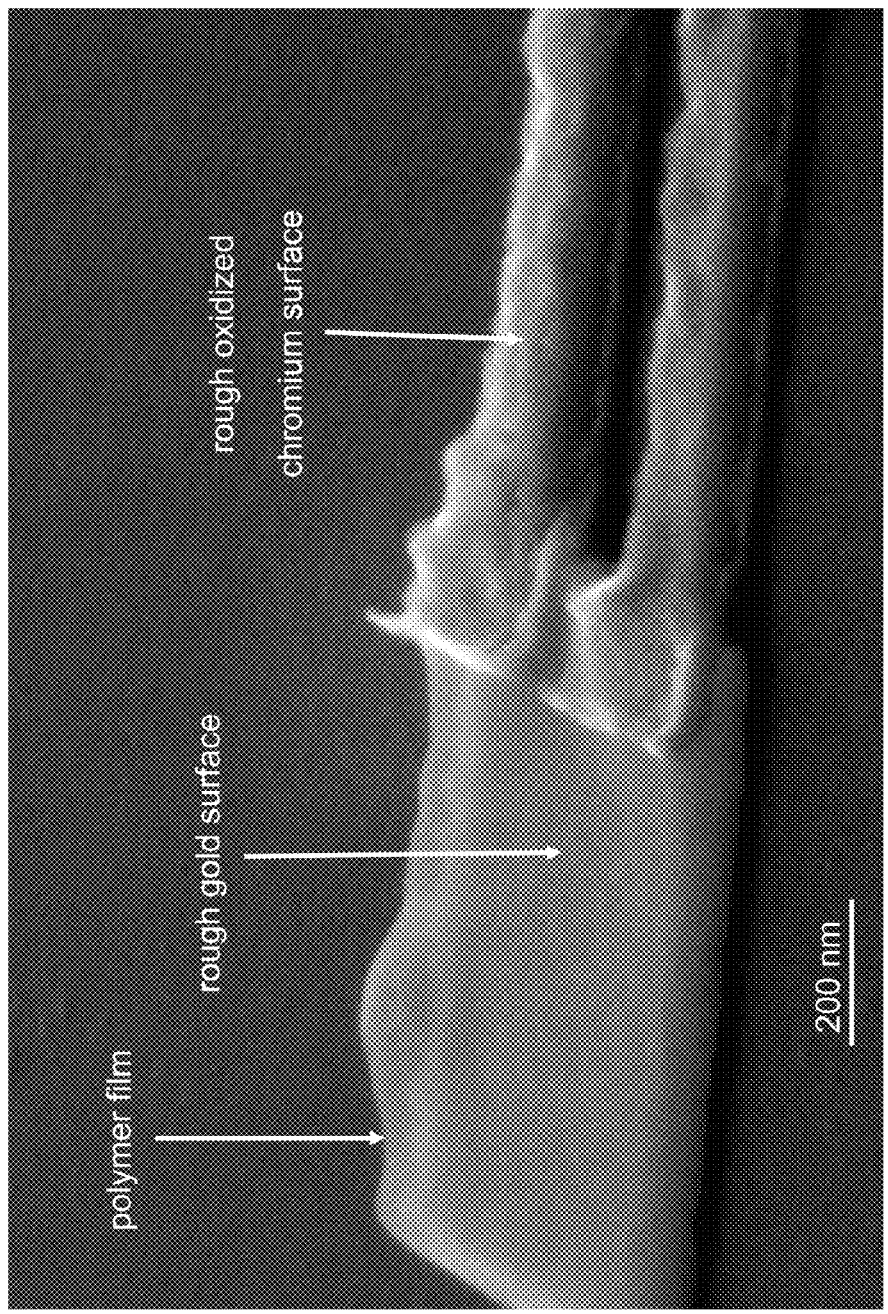
FIG. 7 is a micrograph showing the surface roughness of gold that is visible underneath the translucent polymer film. No translucent film seen on the chromium regions.

FIG. 7 is a micrograph showing the surface roughness of gold that is visible underneath the translucent polymer film. No translucent film seen on the chromium regions.

Sensor Response Measurements

When gold only cantilevers are exposed to solvent vapors, responses to vapors that partition strongly into PMMA are greatly enhanced for cantilevers with a 90 nm thick PMMA film grown by SI-ATRP compared to both bare cantilevers and cantilevers with an approximately 10 nm thick dropcast film of PMMA.

To test the effectiveness of the new coating procedure nanocantilever sensors were exposed to a series of solvent vapors at 2% of their saturated vapor pressures ($P/P_0=2\%$) in a background of laboratory air. Responses were measured after 400 second exposures, with 700 seconds between admissions of two analyte vapors. Responses of cantilevers with significantly different resonance frequencies are compared in the form of the frequency shift ($\Delta F$) divided by the resonance frequency ($F_0$).

The cantilever responses were measured by driving the structures into mechanical resonance using an AC thermoelastic signal, with their resulting motion detected piezoresistively. Measurements were performed using apparatus that has been described in U.S. Pat. No. 7,552,645, which patent is assigned to the assignee of the present application, and which is incorporated by reference herein in its entirety. The combination of drive and motion signals was incorporated into an electronic phase-locked loop (PLL), keeping the cantilever driven at its first flexural mechanical resonance mode frequency. Thus, changes in mode frequency could be monitored in near-real-time. A homebuilt electronics hardware box was used in combination with a PC running a custom LabView data acquisition and control program. The LabView program is available from National Instruments Corporation, 11500 N Mopac Expwy, Austin, Tex. 78759-3504 USA. Sensor data was processed in one of two methods. In the first method, raw frequency trace data was first baseline corrected in using the OriginLab 7.5 Peak Finder Module (available from OriginLab Corporation, One Roundhouse Plaza, Suite 303, Northampton, Mass. 01060 USA). Each sensor response to an analyte exposure was then measured manually by taking the difference between the resonance frequency at the end of the exposure and the baseline resonance frequency. To analyze larger data sets, the raw frequency traces of multiple sensors were imported into MATLAB™ (available from Mathworks, 3 Apple Hill Drive, Natick, Mass. 01760-2098 USA). The frequency trace data was first extracted into small files, each containing a single exposure. Each exposure was then corrected for baseline drift and relative frequency shift measurements were extracted. Custom scripts were used to perform these transformative steps. Sensor response time was determined by running an "open loop" experiment, whereby instead of tracking the nanocantilever resonance frequency with a PLL, cantilevers were driven at a fixed frequency, which allows for more rapid response measurements, but is susceptible to errors at long timescales due to drift. This procedure measures the "true" response time of the cantilevers, unconvoluted by the PLL gain. For all response time measurements, the sensors were exposed to each vapor at least three times at a concentration of 0.02 P/Po. After correcting for baseline drift, the sensor response time was then calculated as the time from the beginning of each response to the point at which the response reaches 90% of its maximum value.

Table II presents a list of solvents used to provide vapors for testing.

TABLE II

| Solvent | Acronym | Formula |
| --- | --- | --- |
| Hexane | Hex | $C_6H_{14}$ |
| Toluene, Methylbenzene | Tol | $C_6H_5CH_3$ |
| Heptane | Hep | $C_7H_{16}$ |
| Ethyl Acetate | EtOAc | $CH_3COOCH_2CH_3$ |
| Chloroform | CHCl3 | $CHCl_3$ |
| Isopropyl Alcohol | IPA | $(CH_3)_2CHOH$ |
| Tetrahydrofuran | THF | $(CH_2)_4O$ |

Figure 8:
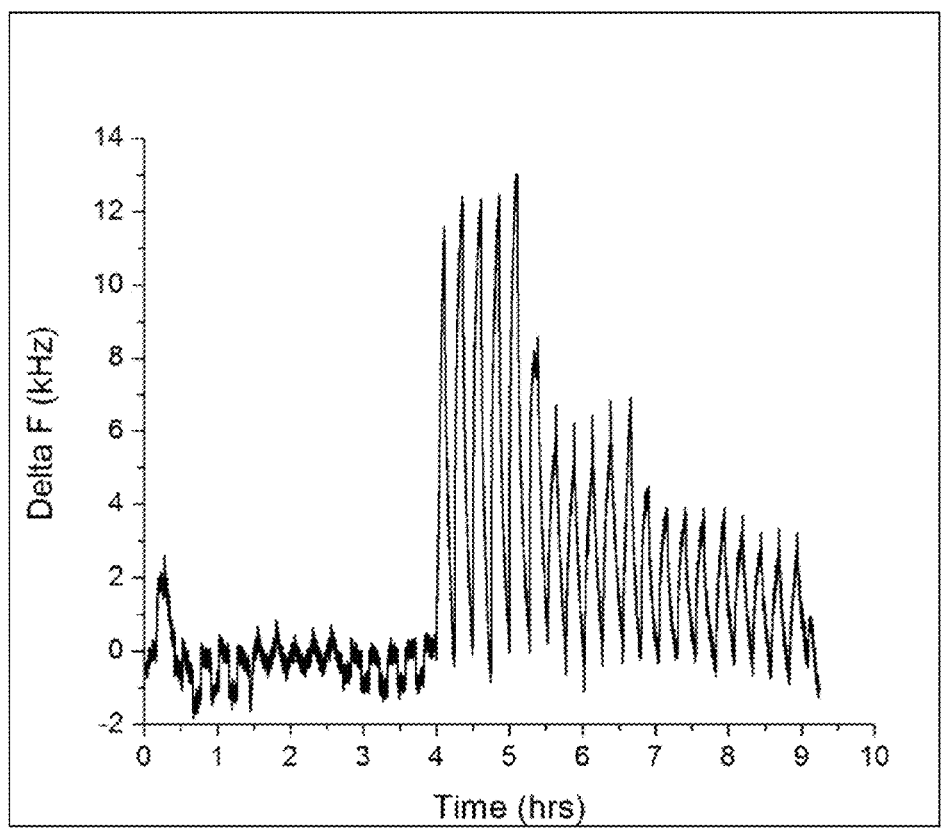
FIG. 8 is a graph showing the raw data (baseline corrected) of sensor responses for a gold only SI-ATRP PMMA coated device to a series of analyte vapors (0.02 P/Po Solvent Vapors) with a background of laboratory air.

FIG. 8 is a graph showing the raw data (baseline corrected) of sensor responses for a gold only SI-ATRP PMMA coated device to a series of analyte vapors (0.02% P/Po solvent vapors) with a background of laboratory air.

Figure 9A:
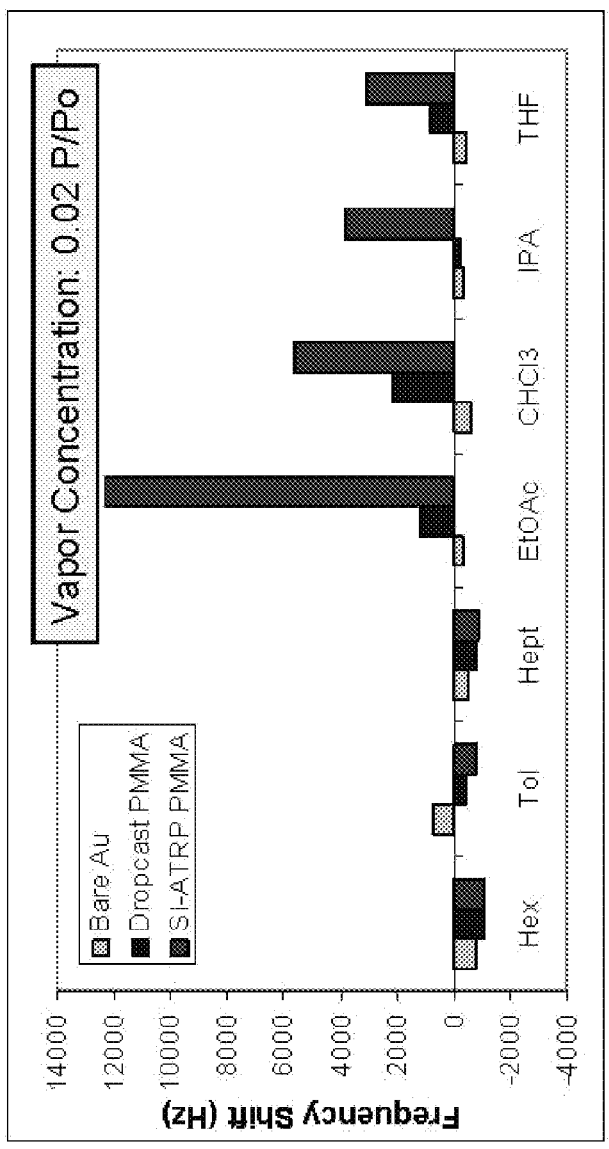
FIG. 9A is a graph that illustrates responses of nanocantilevers having different coatings to a variety of solvent vapors.

FIG. 9A is a graph that illustrates responses of nanocantilevers having different coatings to a variety of solvent vapors. In FIG. 9A, the vertical axis is the response in units of $\Delta F/F_0$. The responses for sensors having bare gold, dropcoated PMMA and SI-ATRP PMMA are shown as sets of three vertical bars (in the stated order) for each solvent identified below the set of three bars.

Figure 9D:
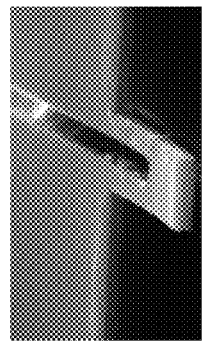
FIG. 9D is an SEM micrograph of a nanocantilever coated with SI-ATRP PMMA
Figure 9C:
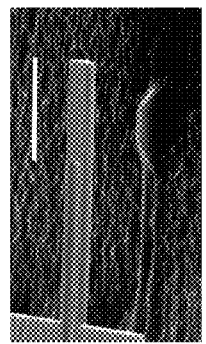
FIG. 9C is an SEM micrograph of a nanocantilever coated with dropcast PMMA. The white bar in the image represents a distance of 1 µm.
Figure 9B:
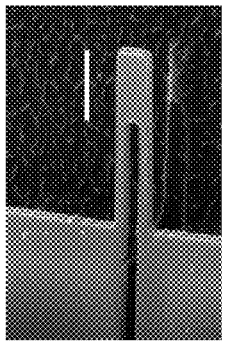
FIG. 9B is an SEM micrograph of a bare gold-coated nanocantilever. The white bar in the image represents a distance of 1 µm.

FIG. 9B is an SEM micrograph of a bare gold coated nanocantilever. The white bar in the image represents a distance of 1 μm.

FIG. 9C is an SEM micrograph of a coated with dropcast PMMA. The white bar in the image represents a distance of 1 μm.

FIG. 9D is an SEM micrograph of a coated with SI-ATRP PMMA

Figure 10A:
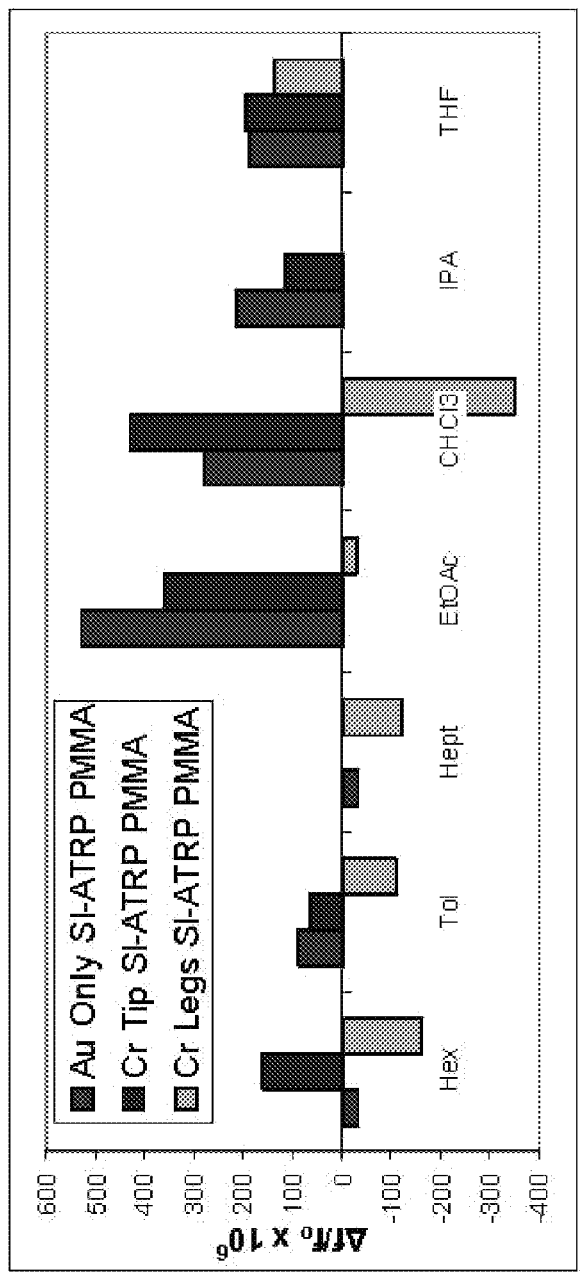
FIG. 10A is a graph showing how localizing polymer film growth to specific cantilever regions changes the sensor response pattern for various vapors.

FIG. 10A is a graph showing how localizing polymer film growth to specific cantilever regions changes the sensor response pattern for various vapors. In FIG. 10A, the vertical axis is the response in units of $\Delta F/F_0$. The responses for sensors having gold coated with SI-ATRP PMMA, sensors with chromium plated at the sensor tip and coated with SI-ATRP PMMA, and sensors having chromium plated on the sensor legs and coated with SI-ATRP PMMA, and are shown as sets of three vertical bars (in the stated order) for each solvent identified below the set of three bars.

Figure 10D:
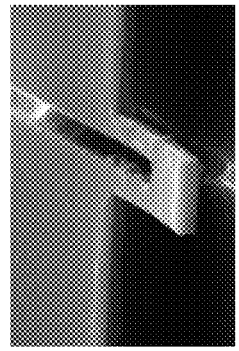
FIG. 10D is a micrograph of a nanocantilever having $f_0=12$ MHz The white bar in the image represents a distance of 100 nm.
Figure 10C:
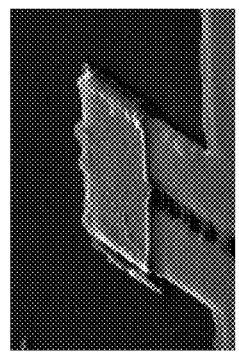
FIG. 10C is a micrograph of a nanocantilever having $f_0=13$ MHz The white bar in the image represents a distance of 200 nm.
Figure 10B:
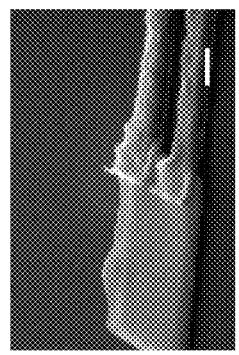
FIG. 10B is a micrograph of a nanocantilever having $f_0=20$ MHz The white bar in the image represents a distance of 200 nm.

FIG. 10B is a micrograph of a nanocantilever having $f_0=20$ MHz The white bar in the image represents a distance of 200 nm.

FIG. 10C is a micrograph of a nanocantilever having $f_0=13$ MHz The white bar in the image represents a distance of 200 nm.

FIG. 10D is a micrograph of a nanocantilever having $f_0=12$ MHz The white bar in the image represents a distance of 100 nm.

Figure 11:
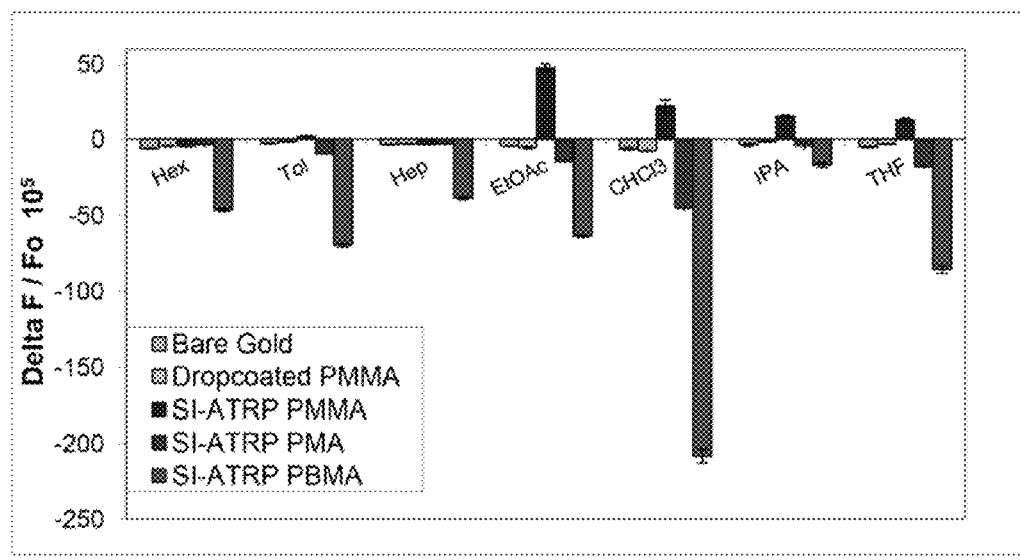
FIG. 11 is a graph showing average responses to various vapors of SI-ATRP PMMA, PMA, and PBMA coated gold-only cantilevers as compared to bare gold and PMMA drop coated cantilevers.

FIG. 11 is a graph showing average $\Delta F/F_0$ responses of bare gold cantilevers and PMMA drop coated cantilevers as compared to SI-ATRP PMMA, SI-ATRP PMA, and SI-ATRP PBMA coated gold-only cantilevers when exposed to various vapors, as listed below the sets of 5 vertical bars. Low Tg polymers PMA and PBMA show mass-loading dominated responses, in contrast to the high Tg polymer, PMMA.

Figure 12:
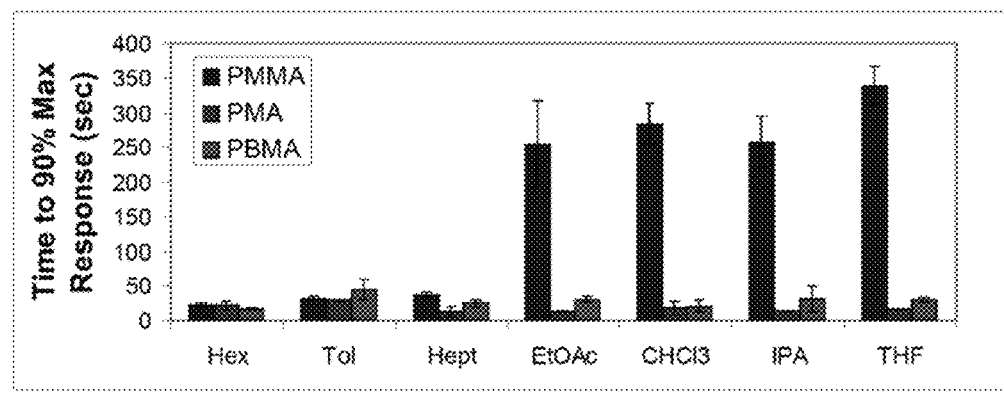
FIG. 12 is a graph showing the time to 90% of the maximum response for PMMA, PMA and PBMA coated nanocantilevers exposed to different vapors.

FIG. 12 is a graph showing the time to 90% of the maximum response for PMMA, PMA and PBMA coated nanocantilevers exposed to different vapors, as listed below the sets of three vertical bars. Low Tg polymers PMA and PBMA respond faster to analyte vapors due to higher coefficients of diffusion than for PMMA.

Figure 13:
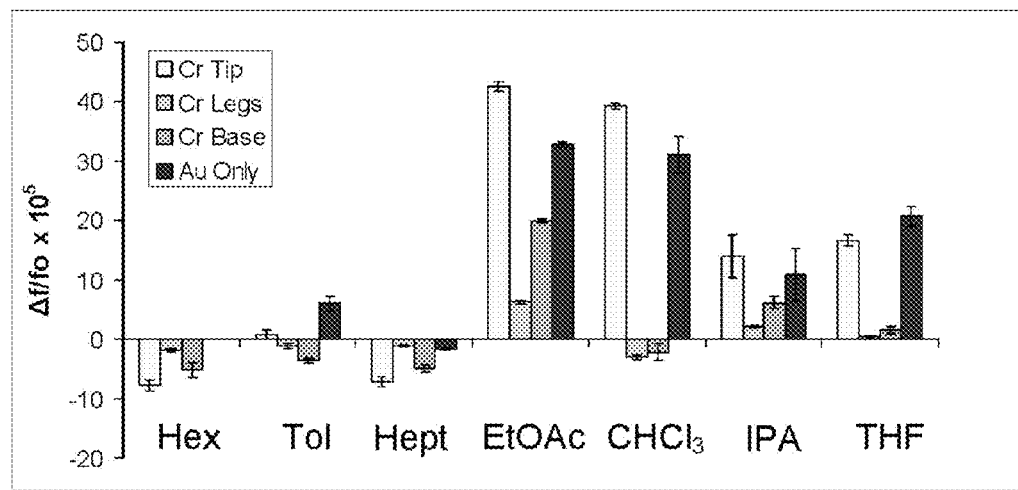
FIG. 13 is a graph showing how localizing polymer film growth to specific cantilever regions changes the sensor response pattern for different vapors that contains the data from FIG. 10A, as well as additional data collected later.

FIG. 13 is a graph showing how localizing polymer film growth to specific cantilever regions changes the sensor response pattern for different vapors. In FIG. 13, the sensors were constructed with chromium-plated tips, chromium plated legs, chromium plated bases, and with gold coating only. The response in units of $\Delta F/F_0$ for vapors as listed below the vertical bars are presented in groups of four bars, in the order described above. The similarity of response between the gold-only cantilever and the Cr tip cantilever indicates that the majority of the observed gold-only cantilever response is due to vapor sorption on the clamped end.

Figure 14:
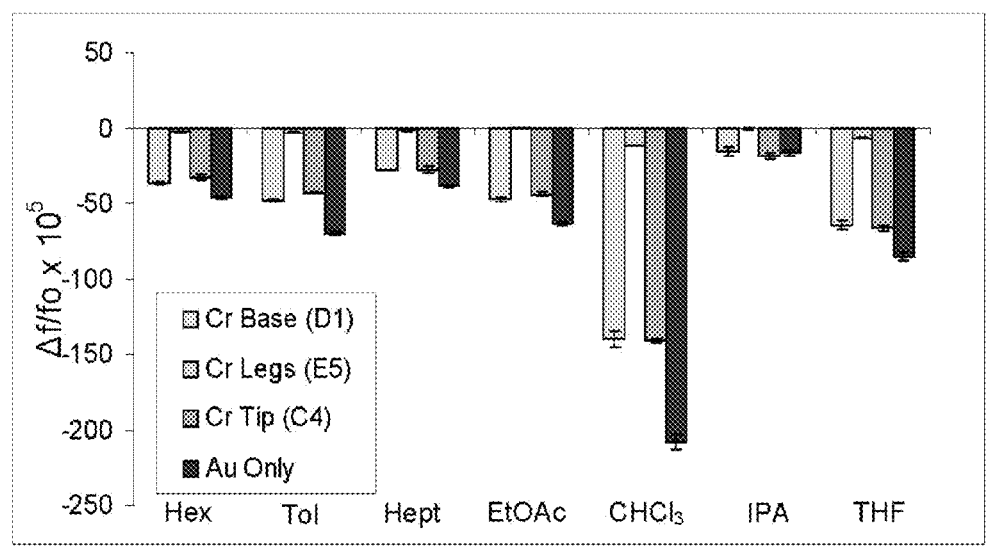
FIG. 14 is a graph showing the response of sensors having localized growth of PBMA in different areas for various vapors. The greater the surface coverage, the stronger the sensor response.

FIG. 14 is a graph showing the response of sensors having localized growth of PBMA in different areas for various vapors. In FIG. 14, the sensors were constructed with chromium-plated bases, chromium plated legs, chromium plated tips, and with gold coating only. The response in units of $\Delta F/F_0$ for vapors as listed below the vertical bars are presented in groups of four bars, in the order described above. One observes that the greater the surface coverage with PBMA polymer, the stronger the sensor response.

DEFINITIONS

As used in this document, the term "promoter" or "promoter film" is intended to mean a layer of the cantilever structure to which a sorbent film is attached. The promoter film is selected from materials that can assist or "promote" the deposition of the sorbent film. In a preferred embodiment, the promoter film is a gold film or layer. In some embodiments the promoter film is fabricated from a material selected from any of: a metal other than gold, such as one of the other noble metals, a metal oxide (examples include aluminum oxide, titanium oxide, iron oxide, indium tin oxide, copper oxide, nickel oxide, zinc oxide, and magnesium oxide), silicon, silicon oxide, other semiconductors (such as GaAs, and Ge treated with HF), carbon (including carbon nanotubes, carbon black particles, diamond, graphite and graphene), a polymer and a clay mineral. See R. Barbey et al., "Polymer Brushes via Surface-Initiated Controlled Radical Polymerization: Synthesis, Characterization, Properties, and Applications," Chem. Rev. 2009, 109, 5437-5527.

As used in this document, the terms "oxidized chromium" means a chromium surface that has been oxidized by any convenient method. In a preferred embodiment, the oxidized chromium is chromium coated with a layer of native oxide. In some embodiments, the chromium is spontaneously oxidized upon exposure to room air. In other embodiments, deliberate exposure of the chromium layer to an oxidizing atmosphere within a deposition system, or deliberate exposure of the chromium to an oxidizing solution, can be employed.

Unless otherwise explicitly recited herein, any reference to an electronic signal or an electromagnetic signal (or their equivalents) is to be understood as referring to a non-volatile electronic signal or a non-volatile electromagnetic signal.

Recording the results from an operation or data acquisition, such as for example, recording results at a particular frequency or wavelength, is understood to mean and is defined herein as writing output data in a non-transitory manner to a storage element, to a machine-readable storage medium, or to a storage device. Non-transitory machine-readable storage media that can be used in the invention include electronic, magnetic and/or optical storage media, such as magnetic floppy disks and hard disks; a DVD drive, a CD drive that in some embodiments can employ DVD disks, any of CD-ROM disks (i.e., read-only optical storage disks), CD-R disks (i.e., write-once, read-many optical storage disks), and CD-RW disks (i.e., rewriteable optical storage disks); and electronic storage media, such as RAM, ROM, EPROM, Compact Flash cards, PCMCIA cards, or alternatively SD or SDIO memory; and the electronic components (e.g., floppy disk drive, DVD drive, CD/CD-R/CD-RW drive, or Compact Flash/PCMCIA/ SD adapter) that accommodate and read from and/or write to the storage media. Unless otherwise explicitly recited, any reference herein to "record" or "recording" is understood to refer to a non-transitory record or a non-transitory recording.

As is known to those of skill in the machine-readable storage media arts, new media and formats for data storage are continually being devised, and any convenient, commercially available storage medium and corresponding read/write device that may become available in the future is likely to be appropriate for use, especially if it provides any of a greater storage capacity, a higher access speed, a smaller size, and a lower cost per bit of stored information. Well known older machine-readable media are also available for use under certain conditions, such as punched paper tape or cards, magnetic recording on tape or wire, optical or magnetic reading of printed characters (e.g., OCR and magnetically encoded symbols) and machine-readable symbols such as one and two dimensional bar codes. Recording image data for later use (e.g., writing an image to memory or to digital memory) can be performed to enable the use of the recorded information as output, as data for display to a user, or as data to be made available for later use. Such digital memory elements or chips can be standalone memory devices, or can be incorporated within a device of interest. "Writing output data" or "writing an image to memory" is defined herein as including writing transformed data to registers within a microcomputer.

"Microcomputer" is defined herein as synonymous with microprocessor, microcontroller, and digital signal processor ("DSP"). It is understood that memory used by the microcomputer, including for example instructions for data processing coded as "firmware" can reside in memory physically inside of a microcomputer chip or in memory external to the microcomputer or in a combination of internal and external memory. Similarly, analog signals can be digitized by a standalone analog to digital converter ("ADC") or one or more ADCs or multiplexed ADC channels can reside within a microcomputer package. It is also understood that field programmable array ("FPGA") chips or application specific integrated circuits ("ASIC") chips can perform microcomputer functions, either in hardware logic, software emulation of a microcomputer, or by a combination of the two. Apparatus having any of the inventive features described herein can operate entirely on one microcomputer or can include more than one microcomputer.

General Purpose Programmable Computers

General purpose programmable computers useful for controlling instrumentation, recording signals and analyzing signals or data according to the present description can be any of a personal computer (PC), a microprocessor based computer, a portable computer, or other type of processing device. The general purpose programmable computer typically comprises a central processing unit, a storage or memory unit that can record and read information and programs using machine-readable storage media, a communication terminal such as a wired communication device or a wireless communication device, an output device such as a display terminal, and an input device such as a keyboard. The display terminal can be a touch screen display, in which case it can function as both a display device and an input device. Different and/or additional input devices can be present such as a pointing device, such as a mouse or a joystick, and different or additional output devices can be present such as an enunciator, for example a speaker, a second display, or a printer. The computer can run any one of a variety of operating systems, such as for example, any one of several versions of Windows, or of MacOS, or of UNIX, or of Linux. Computational results obtained in the operation of the general purpose computer can be stored for later use, and/or can be displayed to a user. At the very least, each microprocessor-based general purpose computer has registers that store the results of each computational step within the microprocessor, which results are then commonly stored in cache memory for later use.

Many functions of electrical and electronic apparatus can be implemented in hardware (for example, hard-wired logic), in software (for example, logic encoded in a program operating on a general purpose processor), and in firmware (for example, logic encoded in a non-volatile memory that is invoked for operation on a processor as required). The present invention contemplates the substitution of one implementation of hardware, firmware and software for another implementation of the equivalent functionality using a different one of hardware, firmware and software. To the extent that an implementation can be represented mathematically by a transfer function, that is, a specified response is generated at an output terminal for a specific excitation applied to an input terminal of a "black box" exhibiting the transfer function, any implementation of the transfer function, including any combination of hardware, firmware and software implementations of portions or segments of the transfer function, is contemplated herein, so long as at least some of the implementation is performed in hardware.

Theoretical Discussion

Although the theoretical description given herein is thought to be correct, the operation of the devices described and claimed herein does not depend upon the accuracy or validity of the theoretical description. That is, later theoretical developments that may explain the observed results on a basis different from the theory presented herein will not detract from the inventions described herein.

Any patent, patent application, or publication identified in the specification is hereby incorporated by reference herein in its entirety. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

While the present invention has been particularly shown and described with reference to the preferred mode as illustrated in the drawing, it will be understood by one skilled in the art that various changes in detail may be affected therein without departing from the spirit and scope of the invention as defined by the claims.

What is claimed is:

1. A cantilever chemical vapor sensor, comprising:
   a cantilever structure having a base, having at least one leg extending from said base and having a tip at a distal end of said at least one leg, said cantilever structure attached to a substrate at said base thereof and configured to oscillate at a natural resonant frequency $F_0$;
   a sorbent film attached to a location of said cantilever structure selected from the group of locations consisting of said base, said at least one leg and said tip, and absent from another of said locations of said cantilever structure selected from the group of locations consisting of said base, said at least one leg and said tip, said sorbent film configured to collect by sorption molecules from a vapor in contact with said cantilever structure, said molecules collected configured to cause a change $\Delta F$ in said natural resonant frequency $F_0$; and
   a signal output port configured to provide a signal representative of said oscillation frequency of said cantilever structure,
   the cantilever chemical vapor sensor further comprising a promoter film and a passivation layer, said promoter film applied to at least two of said locations of said cantilever structure selected from the group of locations consisting of said base, said at least one leg and said tip, and said passivation layer applied over said promoter layer at at least one of said locations of said cantilever structure selected from the group of locations consisting of said base, said at least one leg and said tip.

2. The cantilever chemical vapor sensor of claim 1, wherein said promoter film is a layer of gold.

3. The cantilever chemical vapor sensor of claim 2, wherein a polymerization initiator is present on said layer of gold.

4. The cantilever chemical vapor sensor of claim 1, wherein said sorbent film is a polymer having a glass temperature Tg.

5. A method of fabricating a cantilever chemical vapor sensor according to claim 1, comprising the steps of:
   defining on a surface of a substrate a plurality of regions to be fabricated into the cantilever structure, which cantilever structure when completed comprises the base, the at least one leg extending from said base, and the tip at a distal end of said at least one leg, and the signal output port configured to provide a signal representative of the oscillation frequency of said cantilever structure;
   applying and patterning the promoter layer at two or more of said regions defined as said base, said at least one leg, and said tip;
   overcoating said promoter layer with the passivating layer at at least one of said regions defined as said base, said at least one leg and said tip, while leaving a portion of said promoter layer uncoated;
   etching said substrate so as to fabricate said cantilever structure comprising said base, said at least one leg extending from said base, and said tip at a distal end of said at least one leg, said base of said cantilever structure remaining attached to said substrate and said signal output port;
   depositing the sorbing layer over said uncoated promoter layer while inhibiting said sorbing layer from depositing on said passivating layer;
   said cantilever structure configured to oscillate at a natural resonant frequency $F_0$ in the absence of a sorbate on said sorbing layer and to oscillate at a frequency $F_0+\Delta F$ in the presence of a sorbate on said sorbing layer.

6. The method of fabricating a cantilever chemical vapor sensor of claim 5, wherein said promoter layer comprises gold.

7. The method of fabricating a cantilever chemical vapor sensor of claim 6, further comprising the step of overcoating said gold with a polymerization initiator prior to the step of depositing a sorbing layer over said uncoated promoter layer.

8. The method of fabricating a cantilever chemical vapor sensor of claim 5, wherein said passivating layer comprises chromium.

9. The method of fabricating a cantilever chemical vapor sensor of claim 8, further comprising the steps of oxidizing said chromium and growing a self assembled monolayer of an additional passivating layer on said oxidized chromium prior to the step of depositing a sorbing layer over said uncoated promoter layer.

10. The method of fabricating a cantilever chemical vapor sensor of claim 5, wherein said step of applying and patterning a promoter layer comprises the steps of: depositing a gold layer; and patterning said gold layer.

11. The method of fabricating a cantilever chemical vapor sensor of claim 10, further comprising the step of: applying a polymerization initiator to said patterned gold layer to provide a self assembled monolayer of a substance that promotes deposition of said adsorbing layer at that location.

12. The method of fabricating a cantilever chemical vapor sensor of claim 5, wherein said step of overcoating said promoter layer with the passivating layer comprises the steps of: depositing a chromium layer on a region where deposition of said sorbing layer is to be inhibited; and patterning said chromium layer.

13. The method of fabricating a cantilever chemical vapor sensor of claim 12, further comprising the steps of: oxidizing said chromium layer to provide an oxidized chromium surface; and depositing a self assembled monolayer of a substance that further passivates said oxidized chromium surface to prevent attachment of polymer initiator to that surface.

14. A cantilever chemical vapor sensor, comprising:
a cantilever structure having a base, having at least one leg extending from said base and having a tip at a distal end of said at least one leg, said cantilever structure attached to a substrate at said base thereof and configured to oscillate at a natural resonant frequency $F_0$;
a sorbent film attached to a location of said cantilever structure selected from the group of locations consisting of said base, said at least one leg and said tip, and absent from another of said locations of said cantilever structure selected from the group of locations consisting of said base, said at least one leg and said tip, said sorbent film configured to collect by sorption molecules from a vapor in contact with said cantilever structure, said molecules collected configured to cause a change $\Delta F$ in said natural resonant frequency $F_0$; and
a signal output port configured to provide a signal representative of said oscillation frequency of said cantilever structure;
the cantilever chemical vapor sensor further comprising a passivation layer which comprises oxidized chromium having a self assembled monolayer deposited on said oxidized chromium.

* * * * *